Figure 1A:
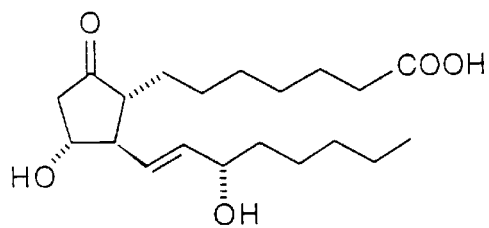
Figure 1A:
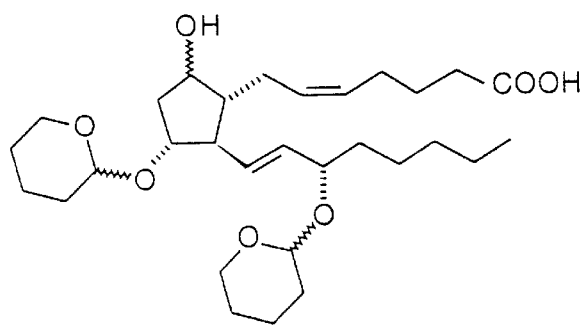
Figure 1A:
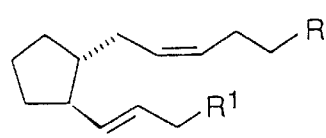
Figure 1A:
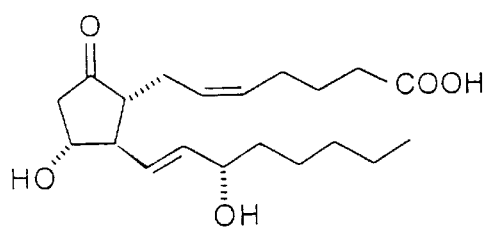
Figure 1A:
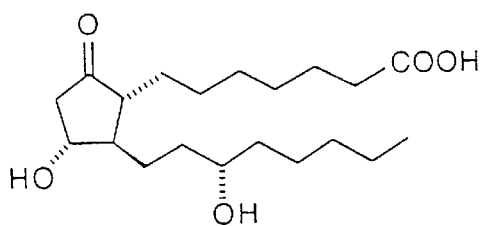

United States Patent [19]
Dalmadi et al.

[11] Patent Number: 6,069,269
[45] Date of Patent: May 30, 2000

[54] PROCESS FOR THE PREPARATION OF PROSTAGLANDIN E1

[75] Inventors: Gyula Dalmadi; Felix Hajdu; Istvan Hermecz, all of Budapest; Karoly Mozsolits, Sopron; Tibor Szabo, Budapest; Zoltan Szeverenyi, Budapest; Ervin Vajda, Budapest, all of Hungary

[73] Assignee: CHINOIN Gyogyszer es Vegyeszeti, Budapest, Hungary

[21] Appl. No.: 09/091,479

[22] PCT Filed: Dec. 18, 1996

[86] PCT No.: PCT/HU96/00078

§ 371 Date: Sep. 18, 1998

§ 102(e) Date: Sep. 18, 1998

[87] PCT Pub. No.: WO97/22581

PCT Pub. Date: Jun. 26, 1997

[30] Foreign Application Priority Data

Dec. 20, 1995 [HU] Hungary ................................ 9503666

[51] Int. Cl.[7] ................................................. C07C 455/00
[52] U.S. Cl. ............................................................ 562/121
[58] Field of Search .............................. 560/703; 562/121

[56] References Cited

U.S. PATENT DOCUMENTS

| | | | |
|---|---|---|---|
| 3,989,736 | 11/1976 | Schaff | 562/503 |
| 4,081,478 | 3/1978 | Nelson | 562/503 |
| 4,085,139 | 4/1978 | Nelson . | |
| 4,122,282 | 10/1978 | Nelson . | |

OTHER PUBLICATIONS

Mai et al., "Prostaglandin E1 and E2 in Bovine Semen: Quantification by Gas Chromatography," Prostaglandins 20:187 (1980).

Slates et al., "A New Stereoselective Total Synthesis of Prostaglandin E1 and its Optical Antipodes", J.C.S. Chem. Comm., pp. 304–305 (1972).
Miyano et al., "Stereoselective Total Synthesis of Prosatag-landin E1", J.C.S. Chem. Comm., pp. 180–181 (1973).
Sih et al., "Total Synthesis of Prostglandins. II. Prostglandin E1", J. Amer. Chem. Soc. 94:10 (1972).
Sih et al., "Total Synthesis of Prosataglandins. IV. A Completely Stereospecific Synthesis of Prostaglandin E1", J. Amer. Chem. Soc. 95:5, pp. 1676–1677 (1973).
"A Total Synthesis of Prostaglandins F1x and E1", J. Org. Chem., vol. 37, No. 18 (1972).
Bengt Samuelsson, Prosatglandins and Related Factors, vol. 239, No. 12, pp. 4091–4096 (1964).
Richard S.P. His, J. of Labelled Compounds and Radiop-harmaceuticals, vol. XIV, No. 4, pp. 515–525 (1978).
Lincoln et al., "Prostanoic Acid Chemistry. II. Hydrogenation Studies and Preparation of 11–Deoxyprostaglandins", J. Org. Chem., vol. 38, No. 5, pp. 951–956 (1973).
Shevchenko et al., "Tritium–Labelling of Natural and Modified Prostaglandins", Journal of Labelled Compounds and Radiopharmaceuticals, vol. XXVII, No. 11, pp. 1243–1255 (1985).
Corey et al., "Total Synthesis of Prostaglandins F1x, E1, F2x, and E2 . . . ", J. Amer. Chem. Soc. 92:8 (1970).
Corey et al., "The Reaction of Diethylalkynylalane Reagents with Conjugated Enones.", J. Amer. Chem. Soc. 93:26 (1971).
Corey et al., "Total Synthesis of Prostaglandins F2x, and E2 . . . ", J. Amer. Chem. Soc. 92:2 (1970).
Corey et al., "Stero–Controlled Synthesis of Prostaglandins F2x, and E2 (d1)", J. Amer. Chem. Soc. 91:20 (1969).

*Primary Examiner*—Robert Gerstl
*Attorney, Agent, or Firm*—Birch, Stewart, Kolasch & Birch, LLP

[57] ABSTRACT

New process for the preparation of prostaglandin E1 of formula (I) starting from the compound of formula (II).

15 Claims, 2 Drawing Sheets

I.

II.

III.

IV.

V.

VI.

VII.

VIII.

PROCESS FOR THE PREPARATION OF PROSTAGLANDIN E1

This application claims the benefit under 35 U.S.C. §371 of prior PCT International Application No. PCT/HU96/00078, which has an International filing date of Dec. 18, 1998, which designated the United States of America, the entire contents of which are hereby incorporated by reference.

Figure 1B:
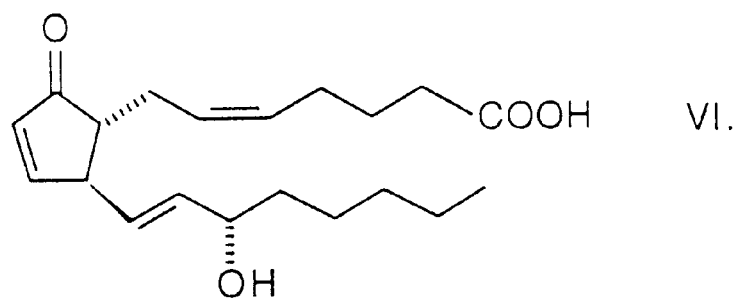
Figure 1B:
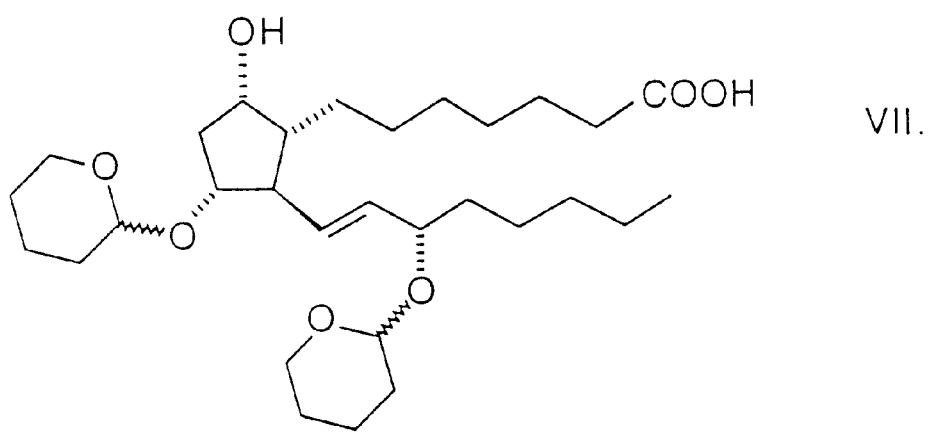
Figure 1B:
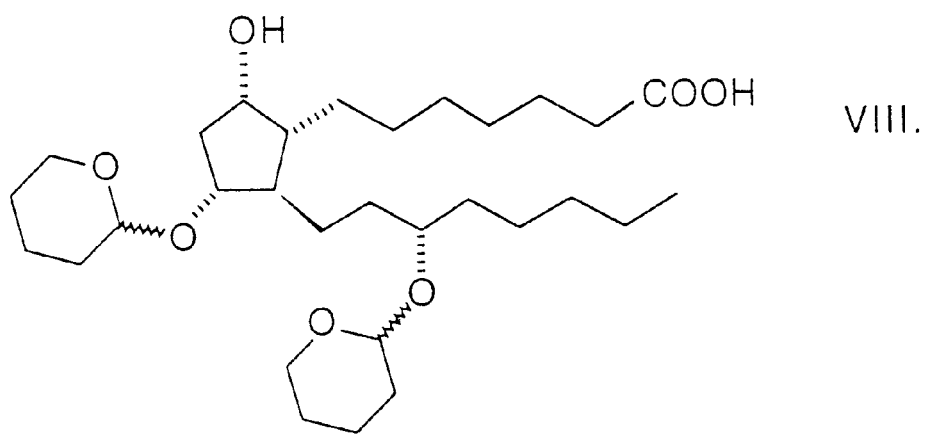

This invention relates to a new process for the preparation of (11 60.13E.15S)-11,15-dihydroxy-9-oxoprost-13-en-1-oic-acid (prostaglandin E1/$PGE_1$) of formula (I) starting from the compound of formula (II). FIGS. 1A and 1B illustrate formulas (I)–(VIII).

Endogen $PGE_1$ plays a significant regulating role in the living organism and it can be used advantageously for the treatment and prevention of diseases of cardiovascular origin.

Biosynthetic PGE1 is formed from dihomo-γ-linolenic acid (Prostaglandin 20, 187, 1980). Several total synthesis of PGE1 has been performed (J. Chem. Soc. Chem. Comm. 304, 1972, J. Chem. Soc. Chem. Comm. 180, 1973, J. Am. Chem. Soc. 94, 3643, 1972: J. Am. Chem. Soc. 95, 1676, 1973, J. Org. Chem. 37, 2921, 1972), the but their industrial realization is very cumbersome. Another possible approach is the regioselective saturation of the cis double bonds of the prostanoid structure of the formula (III) containing cis and trans double bonds. Hydrogenation of 5(Z).11α,13E,15(S)-11,15-dihydroxy-9-oxoprosta-5,13-diene-1-oic-acid ($PGE_2$) of formula (IV) in ethyl acetate yields only 6% of $PGE_1$ of formula (I) (J. Biol. Chem. 239, 4091 1964).

By the application of homogen catalysis at room temperature in case of Wilson type catalyst $PGE_1$ of formula (1) is formed in 72% yield in a 2:3 mixture of benzene and acetone from $PGE_2$ of formula (IV). This reaction is accompanied by formation in significant amounts of the compound of formula (VI) by the elimination of water and of dihydro-$PGE_1$ of formula (V) (J. Labelled Compd. Radiopharm. 14, 515, 1978 and J. Org. Chem 38, 951, 1973). By examining, the hydrogenation of $PGE_2$ of formula (IV) in the presence of ethyl acetate, acetone, benzene, chloroform, methanol and dioxane, catalysts such as palladium on barium sulfate and carbon, platinum on carbon, and nickel and copper on calcium carbonate and Lindlar catalyst, the formed quantity of $PGE_1$ of formula (I) did not exceed 70% and was accompanied by significant amounts of starting $PGE_2$ of formula (IV), dihydro-$PGE_1$ of formula (V) and other prostaglandin derivatives (J. Labelled. Compd. Radiopharm. 27, 1243, 1989) Similar difficulties are encountered if the derivative, containing hydroxyl groups in positions 11 and 15 of $PGE_2$ of formula (IV) is used as the starting material (J. Labelled Compd. Radiopharm. 27, 1243, 1989). Hydrogenation of $PGF_{2a}$ of formula (II) protected by tetrahydropiranyl groups (U.S. Pat. No. 4,085,139; U.S. Pat. No. 4,122,282; J. Am. Chem. SOC. 92, 2586, 1970), and $PGF_{2a}$ derivatives containing other protective groups (J. Am. Chem. Soc. 93, 7319, 1971) has been caried out in ethyl acetate at room temperature and in methanol in the presence of the palladium on carbon catalyst at –20° C. but beside the expected compound of formula (VII) significant quantity of the dihydro derivative of formula (VIII) has also been formed. It is very difficult to separate chromatographically (J. Am. Chem. Soc. 92, 2586, 1970) the non-hydrogenated starting material (e.g. compound of formula (II)) and the reduction products (e.g. compounds of formula (VII) and VIII)).

Thus there remains a need in the art for a regioselective, simple catalytic reduction process for the preparation of PGE1. The present invention is directed to such a regioselective catalytic hydrogenation of the double bond in the 5,6 position selected from the two double bonds, existing in the compound of formula (II), forming a diastomeric mixture in the given case. We intended to achieve such a selectivity beside a minimum of 97% conversion that the purity of the formed compound of formula (VII) should allow its further use without chromatographic purification.

We reached the above goal by an unexpected observation which is the base of our new process. Compound of the formula (II) containing two double bonds can be saturated in positions 5 and 6 with good regioselectivity and appropriate reaction speed in the following way:

The compound of formula (II) is hydrogenated optionally as a diastereomeric mixture in halogenated hydrocarbon solvent and in the presence of a catalyst containing transitional metal and transform the compound of formula (VII) obtained as a diastereomeric mixture in this case to $PGE_1$ of formula (1) with the methods known per se.

The thus prepared $PGF_{1a}$ derivative of formula (VII) can be transformed to the product $PGE_1$ of formula (I) if necessary with known methods such as by the oxidation of the 9-hydroxy group with Jones reagent (J. Am. Chem. Soc. 92, 397, 1970), and by the removal of tetrahydropiranyl protective groups by acidic hydrolysis.

If necessary the sequence of hydrolysis and oxidation steps can be inverted. Transitional metals mean those chemical elements which are defined in Römp's Chemical Lexikon (Müszaki Könyvkiadó Budapest, 1981) on the following pages: volume 1 pages 232–234. In this case preferably multi-phase catalysts containing palladium, platinum, rhodium, rhenium or ruthenium optionally linked to carriers or single-phase catalysts containing compounds of the above listed metals can be used. The metal content of multi-phase catalysts are preferably from 1% to 50% by weight. For halogenated hydrocarbons aromatic, aliphatic or alicyclic hydrocarbons containing one or more fluorine, chlorine, bromine or iodine atoms, can be applied. It is especially preferable to use dichloromethane, 1,2-dichloroethane or 1,2-dichlorobenzene as solvents.

According to our invention in many cases it is advantageous to carry out the hydrogenation in the presence of nitrogen containing basic compounds, for example trialkylamines/preferably triethylamine or diisopropyl-ethyl-amine.

According to the invention the procedure can be done in a wide temperature range, preferably between –20° C. and +40° C. The applied pressure can be atmospheric or higher than atmospheric but it is optimal to work in the pressure range up to 5 bar. Compound of formula (II) and the applied catalyst ratio can be chosen in a wide range but the most advantageous weight ratios are those between 1000:1 and 2:1. Hydrogenation can be done in solutions of different concentrations. It is advantageous to work in solutions having concentrations of 1 to 50 mixed %.

The preparation of starting compound of formula (II) can be carried out by well known methods (J. Amer Chem. Soc. 92 397 (1970), J. Amer. Chem. Soc. 91 5675 (1969)).

The following examples are intended to provide those of ordinary skill in the art with a complete disclosure and description of how to conduct the present synthetic process and are not intended to limit the scope of our claims.

EXAMPLES

Example 1

210 g $PGF_{2a}$ bis-tetrahydropiranyl ether of formula (II) was dissolved in 200 ml 1,2-dichloroethane and 10 g triethylamine and 50 g charcoal containing 10% palladium by weight were added to the reaction mixture. The obtained mixture was stirred under hydrogen pressure of 0.6 bar at room temperature. When no further absorption of hydrogen could be detected the catalyst was filtered cut and the filtrate was extracted with aqueous solution of sodium hydrogen sulfate then with water. After drying the organic phase on water free sodium sulfate the solvents were evaporated. This way we obtained 200 g $PGF_{1a}$ protected by tetrahydropiranyl groups of formula (VII). By introducing ammonia gas into its diisopropyl ether solution, we obtained the ammonium salt of the compound of formula (VII)

Melting point: 65–68° C.

Element analysis based on molecular formula $C_{30} H_{53} NO_7$

| Calculated: | C: 66.45% | H: 9.7% | N: 2.5% |
| Found: | C: 66.3% | H: 9.6% | N: 2.4% |

Example 2

The process was carried our according to Example 1 but the hydrogenation was done at a hydrogen pressure of 2.5 bar and 0° C. and the working up was effected in accordance of Example 1. We obtained 205 g of compound of the formula (VII) which is identical with the product of Example 1.

Example 3

The process was carried our according to Example 2 but diisopropyl ethyl amine was applied instead of triethyl amine and we obtained 210 g of compound of the formula (VII) which is identical with the product of to Example 2.

We claim:

1. A process for the preparation of $PGE_1$ of formula (I)

I.

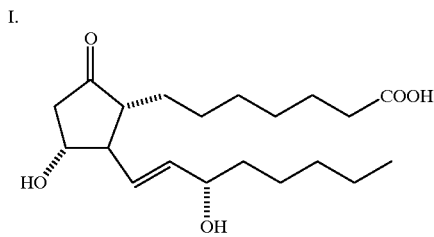

comprising:

hydrogenating the compound of formula (II) optionally as a diastereomeric mixture

II.

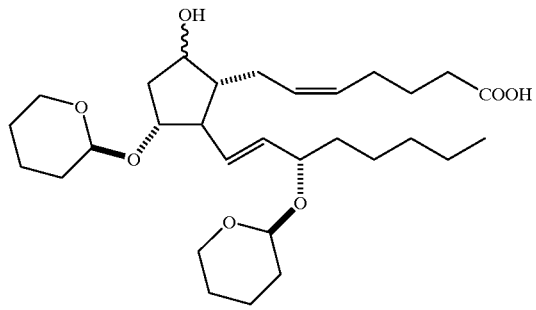

in a halogenated hydrocarbon solvent and in the presence of a catalyst containing one or more transitional metal(s) to transform the compound of formula (II) to a compound of formula (VII)

VII.

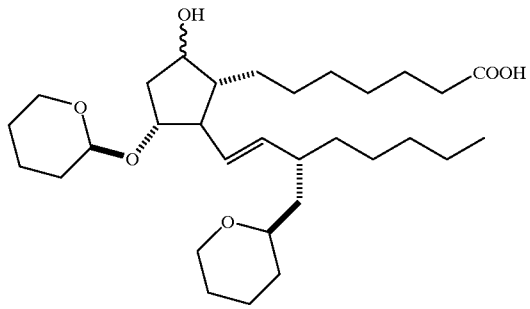

optionally as a diastomeric mixture; and transforming said compound of the formula (VII) to the $PGE_1$ of formula (I).

2. A process according to claim 1 wherein said solvent comprises aliphatic, aromatic or alicyclic hydrocarbon solvents containing one or more chlorine atoms.

3. A process according to claim 1 wherein said catalyst is a multi- phase catalyst.

4. A process according to claim 1 wherein said catalyst is a single- phase catalyst.

5. A process according to claim 1 wherein said process is carried out in the presence of a basic compound containing nitrogen.

6. A process according to claim 1 wherein palladium, platinum, rhodium, rhenium or ruthenium are applied as transitional metal catalysts in a metallic state optionally attached to a carrier or in the form of their compounds.

7. A process according to claim 5 wherein trialkyl amines are used as said nitrogen containing basic compounds.

8. A process according to claim 2 wherein dichloromethane, 1,2-dichloroethane or 1,2-dichlorobenzene is used as said solvent containing one or more chlorine atoms.

9. A process according to claim 1 wherein said catalyst is a palladium on carbon catalyst.

10. A process according to claim 1 wherein hydrogenation is conducted at a hydrogen pressure of between atmospheric pressure and 5 bar.

11. A process according to claim 1 wherein the temperature during hydrogenation is held between −20° C. and +40° C.

12. A process according to claim 1 wherein a mass ratio of compound of formula (II) to said catalyst ranges from 1000:1 to 2:1.

13. A process according to claim 1 wherein hydrogenation is carried out in a solution with concentration of 1 to 50 mix %.

14. The process of claim 7 wherein said amines comprise triethyl amine or diisopropoly-ethyl-amine.

15. A process according to claim 1 wherein palladium, platinum, rhodium, rhenium or ruthenium are applied as transitional metal catalysts in a metallic state optionally attached to a carrier and in the form of their compounds.

* * * * *